United States Patent
Baril et al.

(10) Patent No.: US 11,931,067 B2
(45) Date of Patent: Mar. 19, 2024

(54) INSERTABLE CUTTING GUARDS

(71) Applicant: Covidien LP, Mansfield, MA (US)

(72) Inventors: Jacob C. Baril, Norwalk, CT (US); Saumya Banerjee, Collinsville, CT (US)

(73) Assignee: Covidien LP, Mansfield, MA (US)

( * ) Notice: Subject to any disclaimer, the term of this patent is extended or adjusted under 35 U.S.C. 154(b) by 303 days.

(21) Appl. No.: 17/399,159

(22) Filed: Aug. 11, 2021

(65) Prior Publication Data
US 2022/0047298 A1 Feb. 17, 2022

Related U.S. Application Data

(60) Provisional application No. 63/066,160, filed on Aug. 15, 2020.

(51) Int. Cl.
| | | |
|---|---|---|
| *A61B 1/32* | (2006.01) | |
| *A61B 17/34* | (2006.01) | |
| *A61B 17/00* | (2006.01) | |

(52) U.S. Cl.
CPC .............. *A61B 17/3423* (2013.01); *A61B 2017/00951* (2013.01); *A61B 2017/345* (2013.01)

(58) Field of Classification Search
None
See application file for complete search history.

(56) References Cited

U.S. PATENT DOCUMENTS

| | | | |
|---|---|---|---|
| 5,066,288 A | * | 11/1991 | Deniega ............. A61B 17/3496 604/117 |
| 5,643,283 A | | 7/1997 | Younker |
| 5,741,234 A | * | 4/1998 | Aboul-Hosn ...... A61B 17/3423 604/174 |
| 5,941,873 A | | 8/1999 | Korenfeld |
| 6,059,793 A | | 5/2000 | Pagedas |
| 6,156,055 A | | 12/2000 | Ravenscroft |
| 6,162,209 A | | 12/2000 | Gobron et al. |
| 6,171,317 B1 | | 1/2001 | Jackson et al. |
| 6,206,889 B1 | | 3/2001 | Bennardo |
| 6,224,612 B1 | | 5/2001 | Bates et al. |

(Continued)

OTHER PUBLICATIONS

U.S. Appl. No. 16/883,477, filed May 26, 2020 to Creston et al.
U.S. Appl. No. 16/883,311, filed May 26, 2020 to Baril et al.

*Primary Examiner* — Jan Christopher L Merene
(74) *Attorney, Agent, or Firm* — Carter, DeLuca & Farrell LLP

(57) ABSTRACT

A tissue guard includes an elongated body having a proximal end and a distal end and defining a lumen therethrough. A plurality of torsion springs is included, each torsion spring having a first leg and a second leg and a spring defined therebetween. The first leg of each torsion spring is operably engaged to the distal end of the elongated body. Two or more petals extend from the distal end of the elongated body, each petal is operably engaged to the second leg of one of the torsion springs. The petals are movable between a first, compressed configuration wherein the petals are compressed relative to one another against the bias of the plurality of torsion springs to facilitate insertion of the tissue guard within an access device or natural orifice and a second, expanded configuration to facilitate engagement of the petals beneath the access device or within the natural orifical to secure the tissue guard therein.

16 Claims, 8 Drawing Sheets

(56) References Cited

U.S. PATENT DOCUMENTS

| | | |
|---|---|---|
| 6,228,095 B1 | 5/2001 | Dennis |
| 6,248,113 B1 | 6/2001 | Fina |
| 6,258,102 B1 | 7/2001 | Pagedas |
| 6,264,663 B1 | 7/2001 | Cano |
| 6,270,505 B1 | 8/2001 | Yoshida et al. |
| 6,280,451 B1 | 8/2001 | Bates et al. |
| 6,344,026 B1 | 2/2002 | Burbank et al. |
| 6,350,266 B1 | 2/2002 | White et al. |
| 6,350,267 B1 | 2/2002 | Stefanchik |
| 6,358,198 B1 | 3/2002 | Levin et al. |
| 6,368,328 B1 | 4/2002 | Chu et al. |
| 6,383,195 B1 | 5/2002 | Richard |
| 6,383,197 B1 | 5/2002 | Conlon et al. |
| 6,387,102 B2 | 5/2002 | Pagedas |
| 6,406,440 B1 | 6/2002 | Stefanchik |
| 6,409,733 B1 | 6/2002 | Conlon et al. |
| 6,447,523 B1 | 9/2002 | Middleman et al. |
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,645,283 B2 | 1/2010 | Reynolds et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,901,353 B2 | 3/2011 | Vayser et al. |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinski et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,427,288 B1 | 8/2016 | Chenger et al. |
| 9,468,452 B2 | 10/2016 | Menn et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,629,618 B2 | 4/2017 | Davis et al. |
| 9,642,638 B1 | 5/2017 | Carrier |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 10,076,358 B2 | 9/2018 | Zergiebel et al. |
| 2005/0054993 A1 | 3/2005 | Falahee |
| 2006/0129165 A1* | 6/2006 | Edoga ............ A61B 17/3421 604/174 |
| 2006/0247499 A1* | 11/2006 | Butler ............ A61B 17/3423 600/208 |
| 2011/0021879 A1 | 1/2011 | Hart et al. |
| 2012/0089093 A1 | 4/2012 | Trusty |
| 2012/0289785 A1 | 11/2012 | Albrecht et al. |
| 2013/0204287 A1 | 8/2013 | Mark et al. |
| 2017/0049474 A1 | 2/2017 | Piskun et al. |
| 2017/0340866 A1 | 11/2017 | Richard |
| 2019/0142463 A1 | 5/2019 | Zhu |
| 2020/0367932 A1 | 11/2020 | Baril et al. |
| 2021/0045799 A1 | 2/2021 | Baril et al. |
| 2021/0236194 A1 | 8/2021 | Baril |
| 2021/0236201 A1 | 8/2021 | Baril |
| 2021/0251680 A1 | 8/2021 | Baril et al. |

* cited by examiner

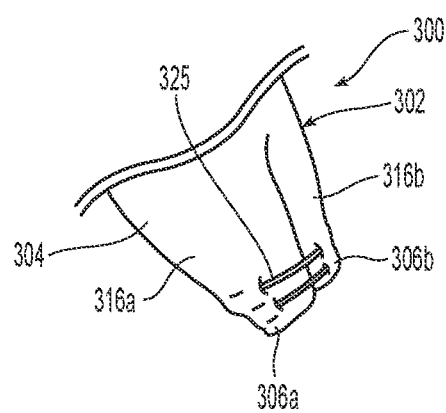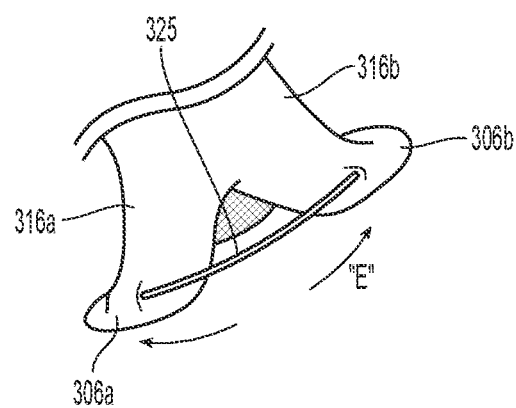
*Fig. 3A*     *Fig. 3B*
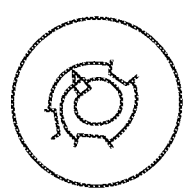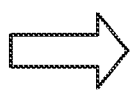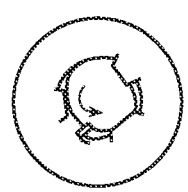
*Fig. 3C*     *Fig. 3D*
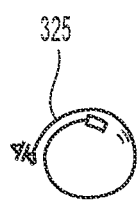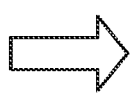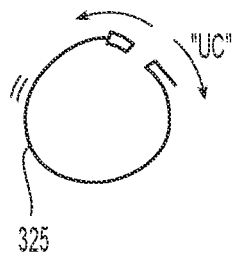
*Fig. 3E*     *Fig. 3F*

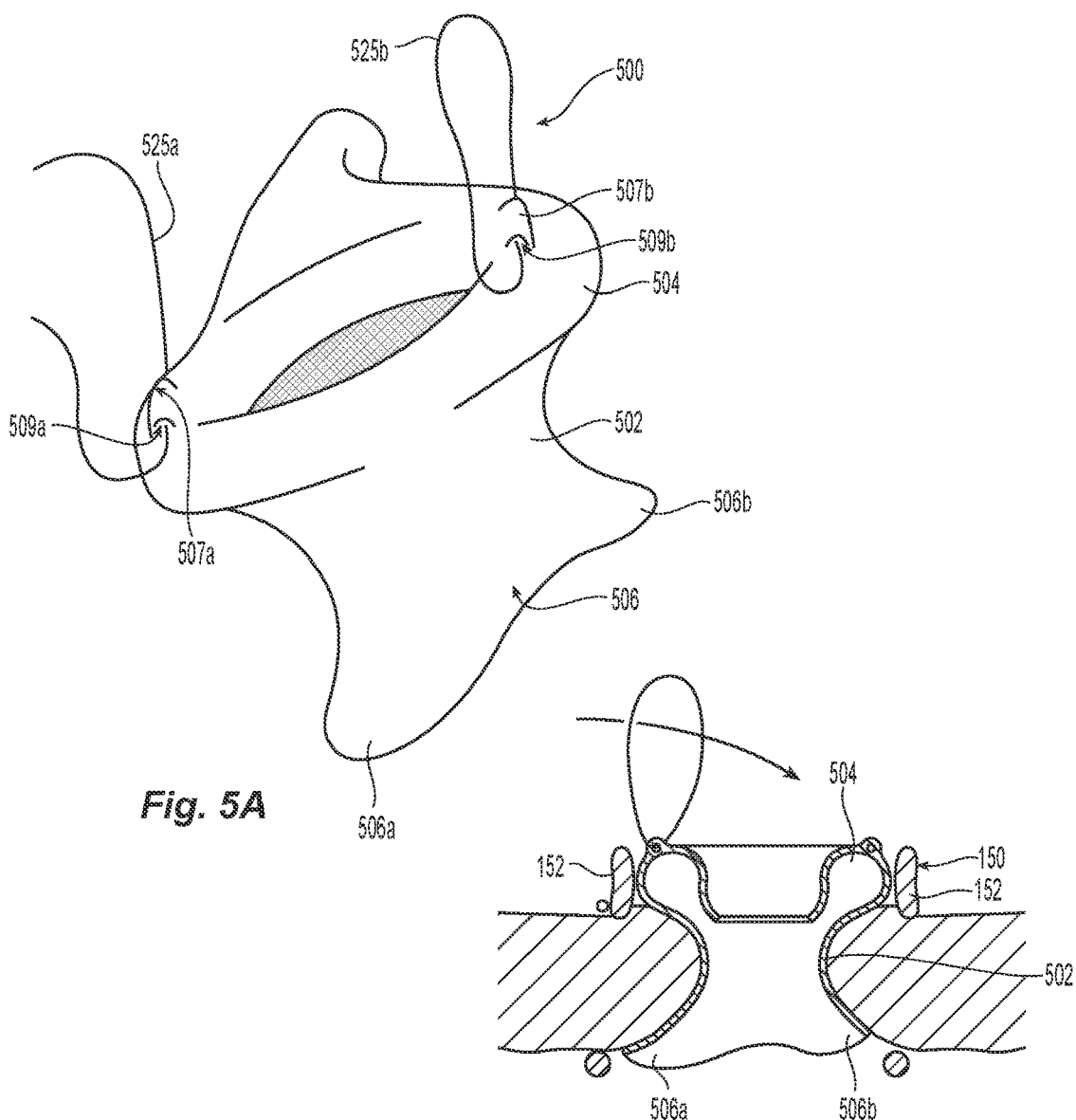
Fig. 5A
Fig. 5B
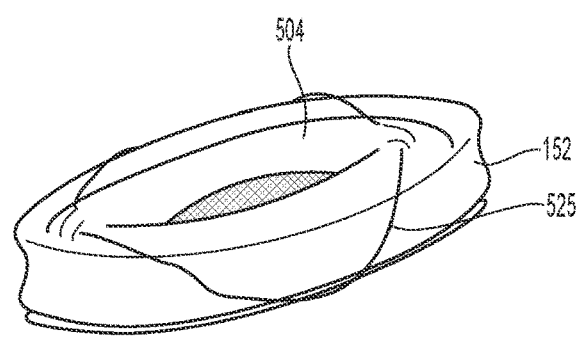
Fig. 5C

INSERTABLE CUTTING GUARDS

CROSS REFERENCE TO RELATED APPLICATIONS

This application claims the benefit of U.S. Provisional Application Ser. No. 63/066,160, filed Aug. 15, 2020, the entire contents of which are incorporated by reference herein.

FIELD

The present disclosure relates to tissue specimen removal and, more particularly, to tissue or cutting guards and systems incorporating the same for use in tissue specimen removal procedures and other electrosurgical surgical procedures.

BACKGROUND

In minimally-invasive surgical procedures, operations are carried out within an internal body cavity through small entrance openings in the body. The entrance openings may be natural passageways of the body or may be surgically created, for example, by making a small incision into which a cannula is inserted.

Minimally-invasive surgical procedures may be used for partial or total removal of tissue from an internal body cavity. However, the restricted access provided by minimally-invasive openings (natural passageways and/or surgically created openings) presents challenges with respect to maneuverability and visualization. The restricted access also presents challenges when large tissue specimens are required to be removed. As such, tissue specimens that are deemed too large for intact removal may be broken down into a plurality of smaller pieces to facilitate removal from the internal body cavity. Typically electrosurgical instruments such as bipolar electrosurgical pencils may be utilized for this purpose.

SUMMARY

As used herein, the term "distal" refers to the portion that is described which is further from a user, while the term "proximal" refers to the portion that is being described which is closer to a user. Further, any or all of the aspects described herein, to the extent consistent, may be used in conjunction with any or all of the other aspects described herein.

Provided in accordance with aspects of the present disclosure is a tissue guard including an elongated body having a proximal end and a distal end and defining a lumen therethrough. A plurality of torsion springs is included, each torsion spring having a first leg and a second leg and a spring defined therebetween. The first leg of each torsion spring is operably engaged to the distal end of the elongated body. Two or more petals extend from the distal end of the elongated body, each petal is operably engaged to the second leg of one of the torsion springs. The petals are movable between a first, compressed configuration wherein the petals are compressed relative to one another against the bias of the plurality of torsion springs to facilitate insertion of the tissue guard within an access device or natural orifice and a second, expanded configuration to facilitate engagement of the petals beneath the access device or within the natural orifical to secure the tissue guard therein.

In aspects according to the present disclosure, one or more of the petals includes a grounding plate operably associated therewith. In other aspects according to the present disclosure, the grounding plate is affixed to one or more petals by a rivet, adhesive or complimentary mechanically interfacing surfaces.

In aspects according to the present disclosure, the first end of one or more of the torsion springs is operably received within a corresponding channel defined within the elongated body. In other aspects according to the present disclosure, the second end of one or more of the torsion springs is operably received within a corresponding channel defined within one of the petals.

In aspects according to the present disclosure, each of the petals is operably engaged to two torsion springs. In other aspects according to the present disclosure, the petals are configured to overlap one another when moved to the first, compressed configuration.

In aspects according to the present disclosure, one or more of the petals is shaped like a duck bill to facilitate insertion within the access device or natural orifice.

Provided in accordance with aspects of the present disclosure is a tissue guard having an elongated body including a proximal end and a distal end and defining a lumen therethrough, the distal end defining two or more petals compressible relative to one another. A coil spring is operably disposed between the petals of the elongated body and is radially transitionable between a first, compressed configuration wherein the distal petals are compressed relative to one another to facilitate insertion of the tissue guard within an access device or natural body orifice and a second, expanded configuration to facilitate engagement of the petals beneath the access device or within the natural orifical to secure the tissue guard therein.

In aspects according to the present disclosure, the coil spring coils within itself upon compression thereof. In other aspects according to the present disclosure, the petals are configured to overlap one another when the coil spring is radially transitioned to the first, compressed configuration.

In aspects according to the present disclosure, one or more of the petals is shaped like a duck bill to facilitate insertion within the access device or natural orifice.

BRIEF DESCRIPTION OF THE DRAWINGS

The above and other aspects and features of the present disclosure will become more apparent in light of the following detailed description when taken in conjunction with the accompanying drawings wherein like reference numerals identify similar or identical elements.

FIGS. 3A-3F show various views of another embodiment of a tissue guard in accordance with the present disclosure including a coil spring;

FIGS. 5A-5C show various views of still another embodiment of a tissue guard in accordance with the present disclosure including an overlapping cinch;

DETAILED DESCRIPTION

Figure 1A:
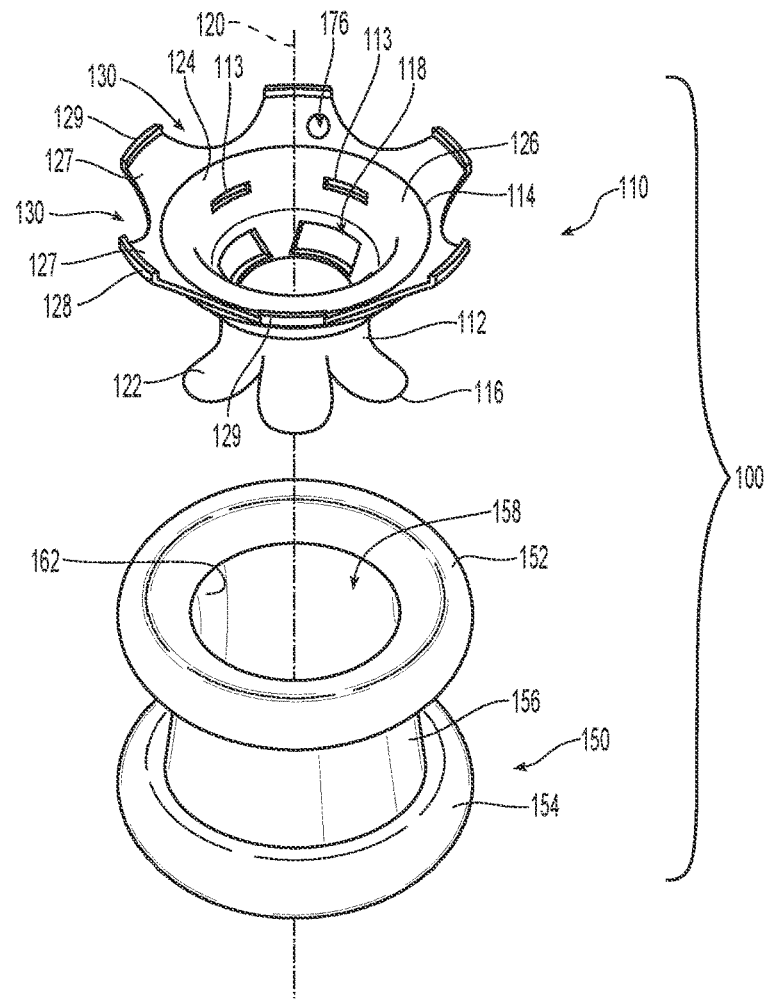
FIG. 1A is an exploded, top, perspective view of a prior art an access device and a tissue guard.
Figure 1B:
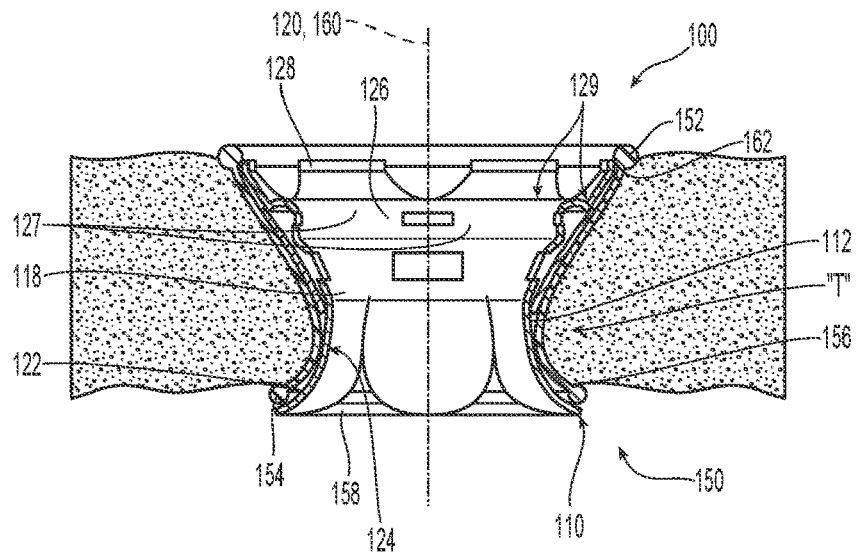
FIG. 1B is a cross-sectional view of the access device and tissue guard of FIG. 1A shown assembled and disposed within an opening in tissue.

Turning to FIGS. 1A and 1B, a prior art system 100 is shown and includes a tissue guard 110 and an access device 150. Tissue guard 110 is monolithically formed as a single piece of material, e.g., a biocompatible plastic such as, for example, polyethylene, polycarbonate, etc., from any suitable method, e.g., injection molding. The material, thickness, and configuration of tissue guard 110 are such that tissue guard 110 defines sufficient stiffness to maintain its shape when positioned within an opening in tissue "T" and/or when engaged within access device 150. However, the material, thickness, and configuration of tissue guard 110 also provide sufficient resilient flexibility to permit manipulation of tissue guard 110 from an at-rest position for insertion into an opening in tissue "T" and/or for engagement within access device 150, with tissue guard 110 returning to or towards the at-rest position after insertion and/or engagement as explained in more detail below. Further, the material, thickness, and configuration of tissue guard 110 is selected such that tissue guard 110 is configured to withstand cutting and puncturing by surgical knives, scalpels, pencils, and the like, thereby protecting surrounding tissue "T" and/or access device 150 from being cut or punctured. Tissue guard 110 may additionally or alternatively be configured to inhibit transfer of thermal and/or electrical energy therethrough to protect surrounding tissue "T" and/or access device 150 from thermal and/or electrical energy.

Continuing with reference to FIGS. 1A and 1B, tissue guard 110 includes a body 112 defining an open proximal end 114, an open distal end 116, and a lumen 118 extending therethrough between open proximal and distal ends 114, 116, respectively. Lumen 118 defines a longitudinal axis 120 and is configured to receive one or more surgical instruments (not shown) therethrough. In embodiments, body 112 defines a funnel-shaped configuration wherein a diameter of body 112 at open proximal end 114 thereof is greater than a diameter of body 112 at open distal end 116 thereof. Additionally or alternatively, the exterior surface 122 of body 112 may define a generally concave configuration while the interior surface 124 of body 112, which defines lumen 118, may define a generally convex configuration. One or more flanges 126 are configured to secure the tissue guard to the access device 150.

Access device 150 may be configured as a tissue retractor, an access port, or other suitable access device configured for positioning within an opening in tissue "T," e.g., a surgical incision or a naturally-occurring orifice, to provide access therethrough into an internal surgical site. Access device 150 includes a proximal rim 152 configured for positioning on an external side of the opening in tissue "T," a distal rim 154 configured for positioning on an internal side of the opening in tissue "T," and a body 156 extending between proximal and distal rims 152, 154, respectively. Body 156 is configured to extend through the opening in tissue "T" and defines a passageway 158 extending longitudinally therethrough to permit access to an internal surgical site through the opening in tissue "T." Passageway 158 defines a longitudinal axis 160. At least a portion of body 156 of access device 150 may be flexible to facilitate insertion and positioning of access device 150 within the opening in tissue "T." In embodiments, body 156 is formed from a flexible sleeve of material including one or more layers of material. Further, access device 150 may be selectively adjustable, e.g., by rolling proximal rim 154 distally about body 156, to retract tissue "T" and/or secure access device 150 within the opening in tissue "T." Access device 150 may further define an inwardly-extending overhang 162 between proximal rim 154 and body 156 and extending annularly about passageway 158.

As shown in FIG. 1B, in use, access device 150 is positioned within an opening in tissue "T" such that, as noted above, distal rim 154 is disposed on an internal surface of tissue "T" on the internal side of the opening in tissue "T," body 156 extends through the opening in tissue "T," and proximal rim 152 is disposed on an exterior surface of tissue "T" on the external side of the opening in tissue "T." As also noted above, access device 150 may be adjusted to conform access device 150 to a patient's anatomy, retracting tissue "T" and/or securing access device 150 within the opening in tissue "T." With access device 150 disposed within the opening in tissue "T," tissue guard 110, led by open distal end 116 thereof, is inserted into passageway 158.

Figure 2A:
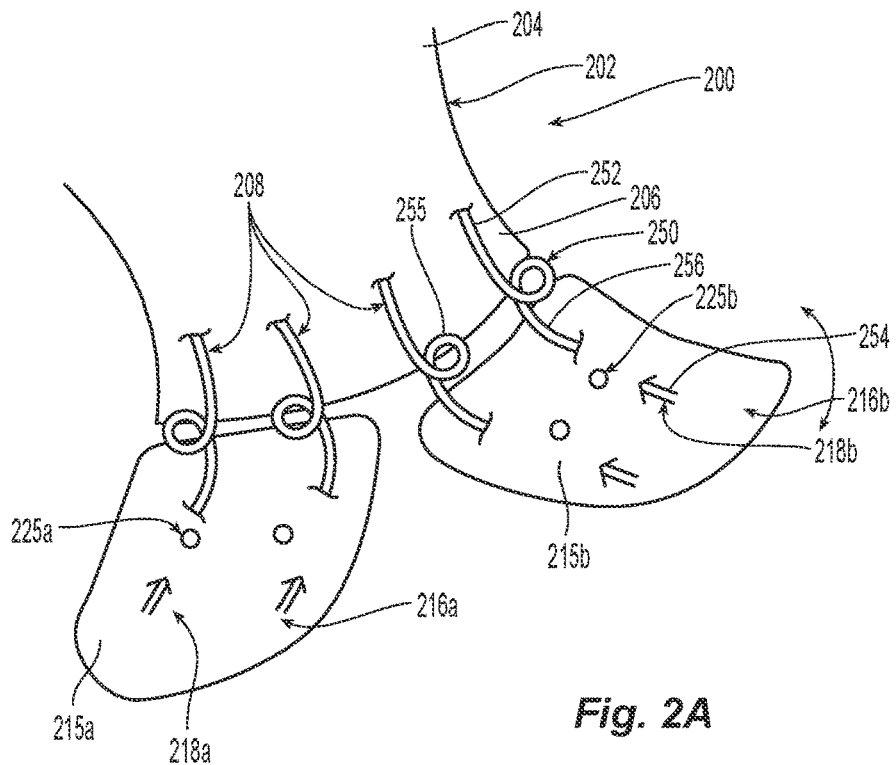
FIG. 2A is a side view of an insertable tissue guard in accordance with the present disclosure shown in an expanded configuration.
Figure 2B:
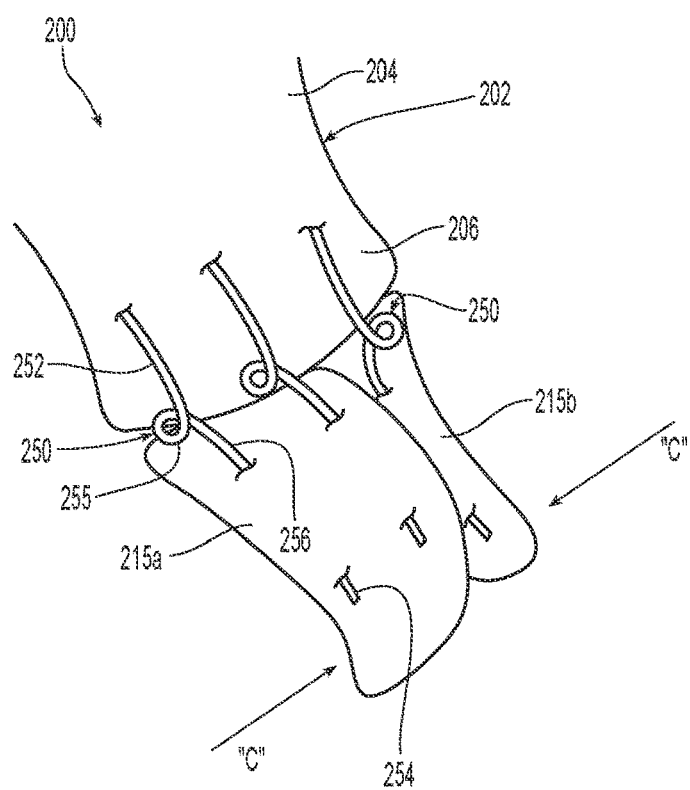
FIG. 2B is a side view of the tissue guard of FIG. 2A shown in a compressed, insertion configuration.
Figure 2C:
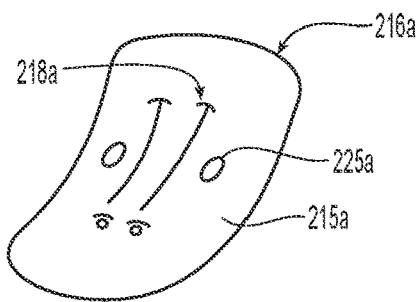
FIGS. 2C-2E are varying views of one of the distal petals of the tissue guard shown in FIG. 2A.

Turning now to FIGS. 2A-2C, one embodiment of a tissue guard for use with an electrosurgical pencil is shown and is generally identified as tissue guard 200. Tissue guard 200 is similar to tissue guard 110 described above and, as such, only those elements that differ are described in detail below. Referenced herein is made to an electrosurgical pencil that is only generally described and only those features necessary for an understanding of the overall system are provided in detail. Cross reference is made to various electrosurgical pencils that may be utilized with system 100, for example, U.S. patent application Ser. No. 16/776,922 filed Jan. 30, 2020, U.S. patent application Ser. No. 16/540,593 filed Aug. 14, 2019, U.S. patent application Ser. No. 16/781,557 filed Feb. 4, 2020 and U.S. patent application Ser. No. 16/789,553 filed Feb. 13, 2020 the entire contents of each of which being incorporated by reference herein.

Tissue guard 200 includes a proximal portion 204 which is configured for engagement with an access device, for example, access device 150, an elongated body portion 202 and a distal end 206 configured for insertion within the access device 150 or direct insertion within an incision "I" in tissue "T". One or more flanges (not shown) may be configured to engage the proximal rim 152 of the access device 150 to secure the tissue guard 200 therein.

Distal end 206 of elongated body 202 is generally oblong and is configured to operably connect to a series of distal petals 216a, 216b. As shown herein, only two petals are disclosed but additional petals may be added depending upon a particular purpose. Each petal 216a, 216b is shaped like a duck bill or a shoe horn to facilitate insertion thereof within the access device 150.

The petals 216a, 216b are operably engaged to the distal end 206 of the elongated body 202 via a plurality of torsions springs 250. Two torsion springs 250 are used with each petal, however, additional (or less) torsions springs 250 may be utilized depending on a particular purpose, e.g., balancing the spring effect of each petal 216a, 216b.

Each torsion spring 250 includes an elongated body 256 having a centrally disposed torsion loop 255 disposed therein and supported at opposite ends by a proximal leg 252 and distal leg 254. The distal leg 254 of each torsion spring 250 is inserted and anchored through a corresponding sleeve or channel 218a, 218b defined within each corresponding petal 216a, 216b. Similarly, the proximal legs 252 of each torsion spring 250 are inserted and anchored through a corresponding number of sleeves or channels 208 defined within the body 202. The torsion springs 250 are biased in an outwardly direction as explained in more detail below. In addition, to facilitate insertion of the cutting guard 200 within the access device 150, the duck bill shape of the distal petals 216a, 216b are configured to overlap one another or partially interleave one another to reduce the insertion profile thereof during insertion.

Figure 2D:
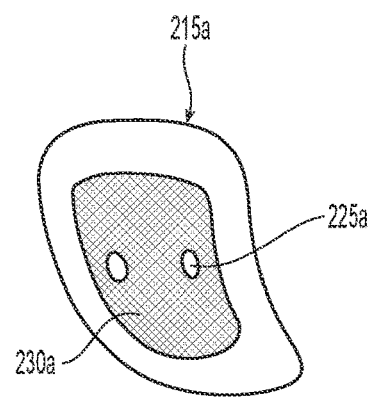
Figure 2E:
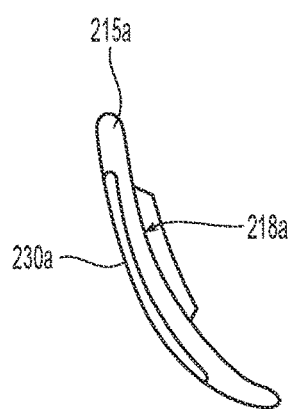

FIGS. 2C-2E show more specific detail of the distal petals, e.g., distal petal 216a. As mentioned above, an outer-facing side of distal petal 216a is shaped like a duck bill or shoe horn to facilitate insertion within access device 150. One or more channels 218a is defined therein for insertion of the distal leg 254 of corresponding number of torsion springs 250. One or more rivets 225a extend through the distal petal 216 that connect to a grounding plate 230a affixed to an underside of the distal petal 216a. Grounding plate 230a and rivets 225a provide a local ground for the electrosurgical pencil (not shown) and may be substantially flush with the outside or underside of the distal petal 216a depending upon a particular purpose. The grounding plate 230a is configured to electrically connect to a remote ground associated with system 100. Cross reference is made to various electrosurgical pencils and grounding systems that may be utilized with system 100, for example, U.S. patent application Ser. No. 16/776,922 filed Jan. 30, 2020, U.S. patent application Ser. No. 16/540,593 filed Aug. 14, 2019, U.S. patent application Ser. No. 16/781,557 filed Feb. 4, 2020, U.S. patent application Ser. No. 16/789,553 filed Feb. 13, 2020, and U.S. patent application Ser. No. 16/883,477 filed May 26, 2020 the entire contents of each of which being incorporated by reference herein.

In use, the user squeezes the distal petals 216a, 216b together against the bias of the torsion springs 250 (in the direction "C") such that the petals 216a, 216b overlap or interleave one another to a reduced profile. The tissue guard 200 is then inserted into the access device 150 and released. Upon release, the distal petals 216a, 216b spring outwardly to engage the underside of the access device 150 in situ. The tissue guard 200 is now secured in place.

During an operation the tissue guard 200 protects the inner periphery of the access device 150 from accidental rupture. Moreover and as explained in detail in the above-identified cross referenced applications, the electrosurgical pencil may be grounded during use simply by contacting the grounding plate 230a disposed within the underside of the petals e.g., petal 216a. To remove the tissue guard 200, the user simply pulls the tissue guard 200 out of the access device 150 by overcoming the outward bias of the torsion springs 250.

FIGS. 3A-3F show another embodiment of a tissue guard generally identified as tissue guard 300 for use with an electrosurgical pencil. Tissue guard 300 is similar to tissue guard 110 described above and, as such, only those elements that differ are described in detail below. Tissue guard 300 includes an elongated body 302 having a proximal end 304 and at least a pair of petals 316a, 316b disposed at a distal portion thereof. As shown herein, only two petals are shown but additional petals may be added depending upon a particular purpose. Each petal 316a, 316b is shaped like a duck bill or a shoe horn to facilitate insertion thereof within the access device 150. The two petals 316a, 316b are configured to overlap one another or partially interleave one another to reduce the insertion profile thereof during insertion.

Each petal 316a, 316b includes a respective distal end 306a, 306b that may be compressed relative to one another to facilitate insertion into access device 150. A coiled wire or spring 325 connects each petal at a distal end thereof and, when the petals are compressed, the coil wraps inwardly around itself (e.g., compresses radially) under an outward bias (FIGS. 3A, 3C, and 3E). The ability of the petals 316a, 316b to interleave or overlap one another facilitates the reduction of the insertion profile of the tissue guard 300 simplifying insertion into the access device 150.

Once inserted, the coiled wire 325 urges the petals 316a, 316b outwardly to engage the underside of the distal end of the access device 150 in situ (FIGS. 3B, 3D). The tissue guard 300 is now secured in place. During an operation the tissue guard 300 protects the inner periphery of the access device 150 from accidental rupture. To remove the tissue guard 300, the user simply pulls the tissue guard 300 out of the access device 150 by overcoming the outward bias of the coiled wire 325 allowing the coiled wire 325 to re-coil onto itself as the petals 316a, 316b interleave one another.

FIGS. 4A-4E show another embodiment of a tissue guard generally identified as tissue guard 400 for use with an electrosurgical pencil. Tissue guard 400 is similar to tissue guard 110 described above and, as such, only those elements that differ are described in detail below. Tissue guard 400 includes an elongated body 402 having a proximal end 404 and a distal end 406. Distal end 406 is substantially resilient and is foldable onto itself to reduce the overall profile thereof to facilitate insertion of the distal end 406 into the access device 150.

A donut-like balloon 425 is affixed to distal end 406 and is expandable from a deflated configuration for insertion into the access device 150 and an inflated configuration for retention within the access device 150. More particularly, when the balloon 425 is deflated, the balloon 425 reduces the overall profile of the distal end 406 to a minimum configuration to facilitate insertion within the access device 150. The resiliency of the distal end 406 allows the distal end 406 to fold upon itself to reduce the overall profile thereof. Once inserted within the access device 150, the balloon 425 is inflated to expand beneath the access device 150 and secure the tissue guard 400 therein. To remove the tissue guard 400, the balloon 425 is simply deflated to disengage the balloon 425 from underneath the access device 150 and to allow for removal.

Figure 4A:
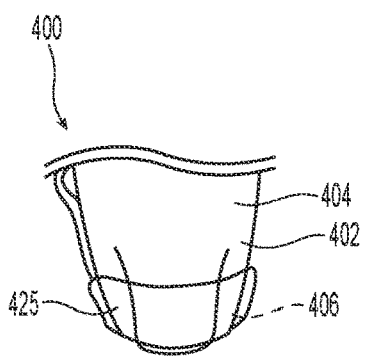
FIGS. 4A-4E show various views of yet another embodiment of a tissue guard in accordance with the present disclosure including a balloon.
Figure 4B:
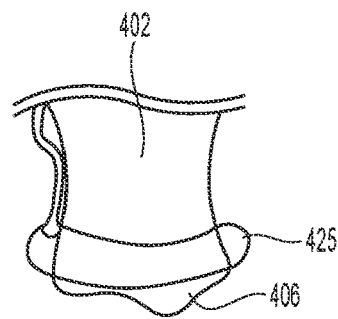
Figure 4C:
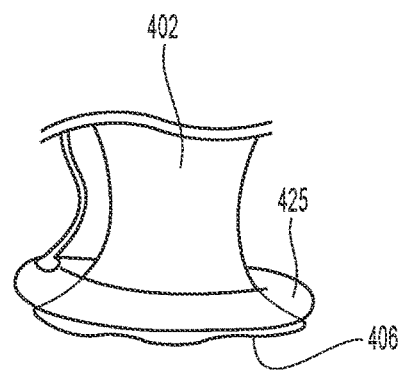
Figure 4D:
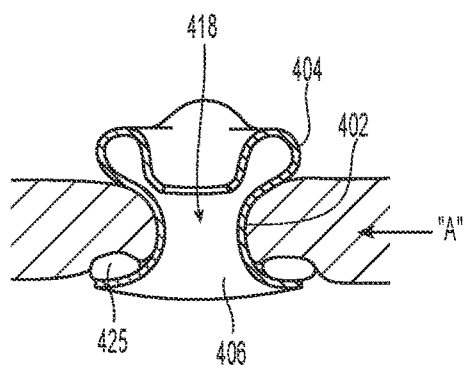
Figure 4E:
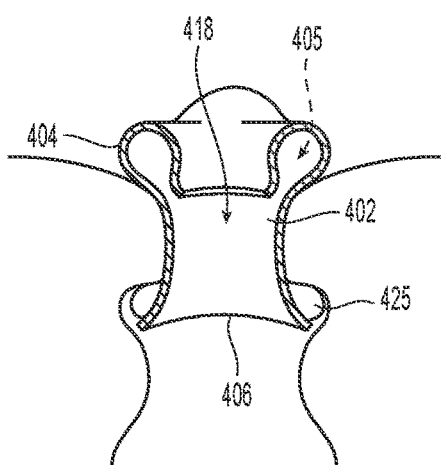

FIGS. 4D and 4E show a version of the tissue guard 400 for use without an access device 150. In this instance, the tissue guard 400 is placed within an incision when the balloon 425 is disposed in a deflated state. Once inserted, the balloon 425 is inflated to engage the underside of the surgical cavity, e.g., abdominal cavity "A", to secure the tissue guard in situ. The proximal end 404 may include a resilient ring (not shown) or additional inflatable cavity 405 to secure the proximal end 404 of the tissue guard 400 outside the incision (FIG. 4D). The tissue guard 400 may be secured within a vaginal canal in much the same manner (FIG. 4E).

FIGS. 5A-5C show another embodiment of a tissue guard generally identified as tissue guard 500 for use with an electrosurgical pencil. Tissue guard 500 is similar to tissue guard 110 described above and, as such, only those elements that differ are described in detail below. Tissue guard 500 includes an elongated body 502 having a proximal end 504 and a distal end 506. Distal end 506 is substantially resilient and malleable to reduce the overall profile thereof to facilitate insertion of the distal end 506 into the access device 150. Distal end 506 is generally shoe horn shaped and includes a long petal 506a on one side thereof and a short petal 506b on an opposite side thereof to facilitate insertion of the tissue guard 500 into the access device 150 and an internal body cavity "A" (FIGS. 5A and 5B). Prior to insertion, short petal 506b may be inverted into body 502 such that only the long petal 506a remains exposed for insertion (FIG. 5B) such as described in commonly-owned U.S. application Ser. No. 16/883,311 filed May 26, 2020 the entire contents of which being incorporated by reference herein.

Proximal end 504 includes one or more channel loops, e.g., channel loops 507a, 507b, that define a corresponding number of passageways therethrough, e.g., passageways 509a, 509b, configured to secure a corresponding number of sutures (or other elastic material) 525a, 525b therein. Sutures 525a, 525b may be in the form of an elastic loop or may be cinchable to size the sutures 525a, 525b as needed during use.

In use, the tissue guard 500 is inserted within the access device 150 as shown in FIG. 5B. The shoe-horn shape of the long petal 506a secures the tissue guard 500 under the distal end 154 of the access device 150 while the proximal end 504 lies relatively flush with the proximal end 152 of the access device 150. Once seated within the access device 150, each respective suture loop 525a, 525b is pulled across the top of the proximal end 504 to engage the opposite underside of the proximal end 152 of the access device 150 (FIG. 5C). The suture loops 525a, 525b may be stretched or cinched to accommodate as needed. The tissue guard 500 is now secured for use.

To disengage the tissue guard 500, the suture loops 525a, 525b are disengaged from the opposite side of the proximal end 152 of the access device 150 and the tissue guard 500 is then pulled out of the access device 150. The tissue guard 500 may need to be pulled in a reverse shoe horn-like manner to facilitate disengagement from the access device 150.

FIGS. 6A-6D show another embodiment of a tissue guard generally identified as tissue guard 600 for use with an electrosurgical pencil. Tissue guard 600 is similar to tissue guard 110 described above and, as such, only those elements that differ are described in detail below. Tissue guard 600 includes an elongated body 602 having a proximal end 604 and a distal end 606. Distal end 606 is substantially resilient and malleable to reduce the overall profile thereof to facilitate insertion of the distal end 606 into the access device 150. Distal end 606 is generally shoe horn shaped and includes a long petal 606a on one side thereof and a short petal 606b on an opposite side thereof to facilitate insertion of the tissue guard 600 into the access device 150 and/or an internal body cavity "A" (FIGS. 5A and 5B). Prior to insertion, short petal 606b may be inverted into body 602 such that only the long petal 606a remains exposed for insertion (FIG. 5B) such as described in commonly-owned U.S. application Ser. No. 16/883,311 filed May 26, 2020 the entire contents of which being incorporated by reference herein.

Proximal end 604 is annular ring shaped and includes a connection to a surgical evacuation port 609 that connects to a surgical evacuation system (not shown). Proximal end 604 also includes a plurality of hooks, e.g., hooks 625a, 625b, that are configured to engage a corresponding elastic loop or cinch 650 to secure the tissue guard 600 to the access device 150.

Figure 6A:
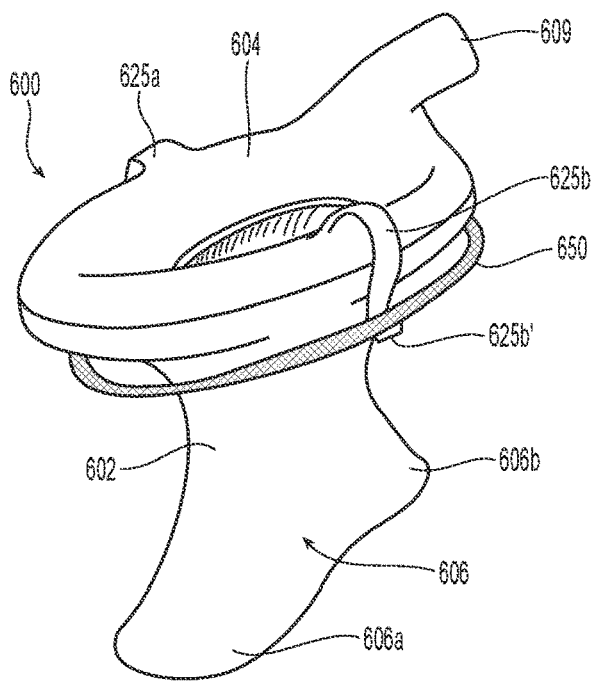
FIGS. 6A-6D show various views of another embodiment of a tissue guard in accordance with the present disclosure including opposing retaining flanges.
Figure 6B:
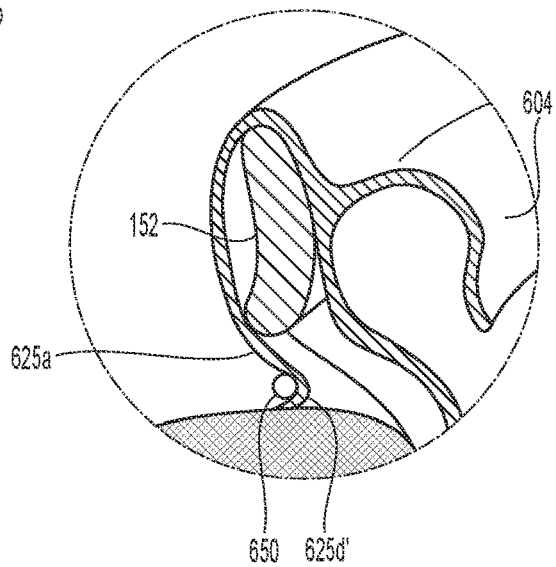

More particularly, each hook 625a, 625b is integrally (or otherwise affixed) to the proximal end 604 and extends therefrom to a position below the proximal end 604 and proximate the skin. Each hook 625a, 625b includes a respective distal flange, e.g., distal flange 625b', that is configured to securely engage the elastic loop or cinch 650. Once the tissue guard 600 is positioned within the access device 150, the elastic loops or cinches 650 are positioned over respective sides of the proximal end 604 of the access device 150 and positioned to engage the respective distal flanges 625a', 625b' of the hooks 625a, 625b. The elasticity of the elastic loops or cinches 650 (or by re-positioning or cinching the cinches 650 as explained in more detail below) biases the elastic loops or cinches 650 against and/or underneath the proximal rim 152 of the access device 150 securing the tissue guard 600 thereon (FIG. 6B).

Figure 6C:
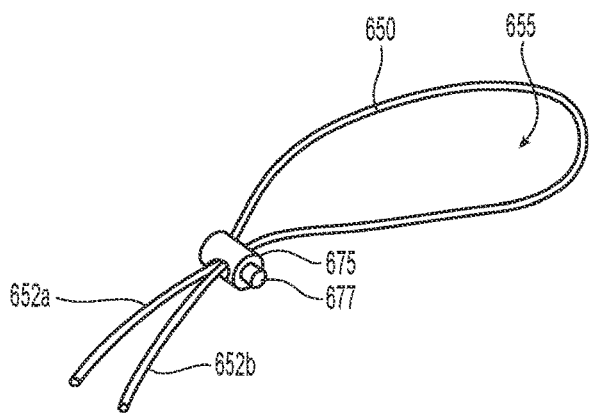
Figure 6D:
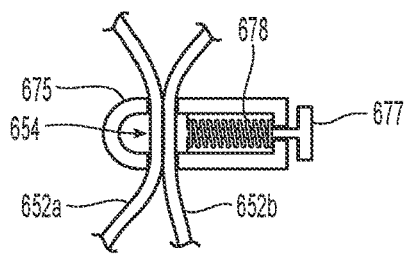

An example of a contemplated cinch 650 is shown in FIGS. 6C and 6D. More particularly, the cinch 650 includes a loop 655 having opposing ends 652a and 652b. Each end 652a, 652b is fed through a cinching mechanism 675 including a release post 677, a spring 678 and a passageway 654 defined to receive opposite ends 652a, 652b. Opposite ends 652a, 652b are fed through the cinching mechanism 675 to form the loop 655. The release post 677 is selectively positionable (e.g., pull-able) between a first position that allows the ends 652a, 652b to be fed through the cinching mechanism 675 and re-positioned (e.g., tightened or released as needed) and a second or biased position that secures the ends 652a, 652b in place (FIG. 6D). Spring 678 biases the cinching mechanism 675 in the second position and release post 677 releases the ends for re-positioning as needed.

FIGS. 7A-7E show another embodiment of a tissue guard generally identified as tissue guard 700 for use with an electrosurgical pencil. Tissue guard 700 is similar to tissue guard 110 described above and, as such, only those elements that differ are described in detail below. Tissue guard 700 includes an elongated body 702 having a proximal end 704 and a distal end 706. Distal end 706 is substantially resilient and malleable to reduce the overall profile thereof to facilitate insertion of the distal end 706 into the access device 150. Distal end 706 is generally shoe horn shaped and includes a long petal 706a on one side thereof and a short petal 706b on an opposite side thereof to facilitate insertion of the tissue guard 700 into the access device 150 and an internal body cavity "A" (FIGS. 5A and 5B). Prior to insertion, short petal 706b may be inverted into body 702 such that only the long petal 706a remains exposed for insertion (FIG. 5B) such as described in commonly-owned U.S. application Ser. No. 16/883,311 filed May 26, 2020 the entire contents of which being incorporated by reference herein.

Proximal end 704 of the tissue guard 700 is generally donut-shaped and made from a resilient material that permits it to flex as need to accommodate instrument therein. The tissue guard 700 may be configured as a stand alone unit or may be configured to operably engage the access device 150 in any of the manners described above. The stand along configuration is described below.

Figure 7A:
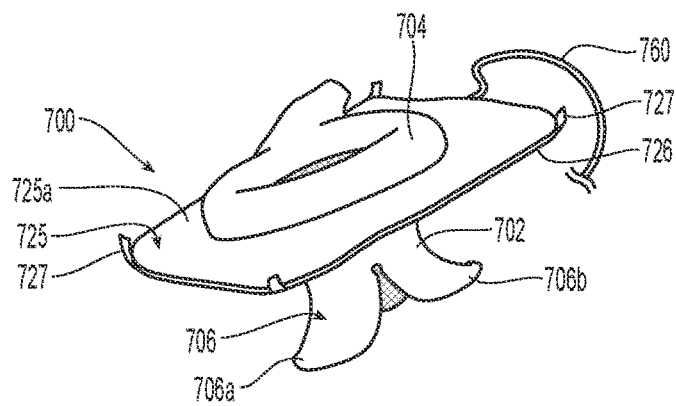
FIGS. 7A-7E show various views of yet another embodiment of a tissue guard in accordance with the present disclosure including an adhesive grounding plate.
Figure 7B:
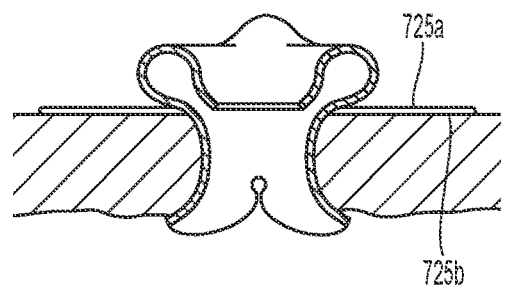

The proximal end 704 of the tissue guard 700 is configured for operable engagement with an adhesive panel 725 disposed on an underside thereof. More particularly, adhesive panel 725 includes an upper surface 725a and a tissue-engaging surface 725b that is configured to adhesively (or otherwise) engage the skin of the patient proximate the incision or natural orifice (FIG. 7B). A backer material 726 covers the tissue-engaging surface 725b to allow positioning the tissue guard 700 prior to securing the tissue guard 700 to the patient.

Figure 7C:
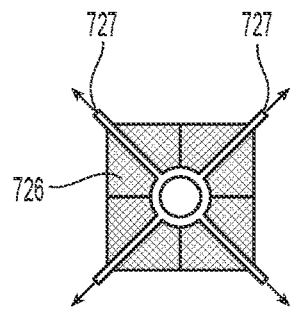
Figure 7D:
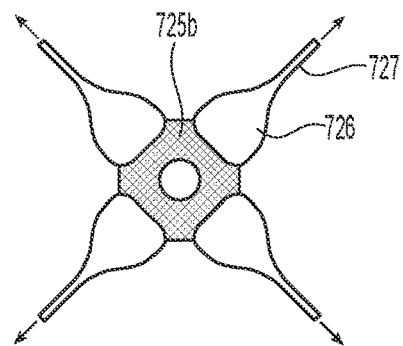
Figure 7E:
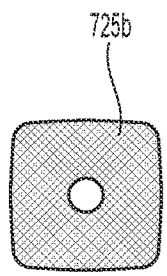

In use, the tissue guard 700 is positioned within the adhesive panel 725 (or the tissue guard 700 comes assembled in this fashion) and inserted into the incision or natural orifice (FIG. 7B). The user then peels the backer material 726 off of the adhesive panel 725 by pulling tabs 727 (FIGS. 7C and 7D). This secures the tissue guard 700 in place proximate the incision or natural orifice.

In embodiments, a second backer material (not shown) may be utilized. More particularly, in this embodiment, the elongated body 702, proximal end 704 and distal end 706 are separate from the adhesive panel 725. The user positions the adhesive panel 725 proximate the incision in the manner described above without the elongated body 702, proximal end 704 or distal end 706, by peeling off the backer material 726. The user then peels away a second backer panel revealing another adhesive material (not shown) atop surface 725a. The user then inserts the distal end 706 and elongated body 702 through the adhesive panel 725 and the proximal end 704 operably engages the second adhesive to secure the tissue guard 700 thereon.

In embodiments, the upper surface 725 may be composed of an electrically conductive material and connected to an electrical ground (not shown). More particularly, the upper surface 725a may be operably engaged to an auxiliary lead 760 that operably and electrically connects to an auxiliary electrosurgical return (not shown) or electrosurgical generator (not shown). As such, the user can ground the electrosurgical instrument, e.g., electrosurgical pencil, as needed during use thereof.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue guard, comprising:
   an elongated body including a proximal end and a distal end and defining a lumen through the elongated body;
   a plurality of torsion springs, each torsion spring including a first leg and a second leg and a spring defined between the first and second legs, the first leg of each torsion spring operably engaged to the distal end of the elongated body; and
   at least two petals extending from the distal end of the elongated body, each petal operably engaged to the second leg of at least one torsion spring of the plurality of torsion springs, wherein the petals are movable between a first, compressed configuration wherein the at least two petals are compressed relative to one another against the bias of the plurality of torsion springs to facilitate insertion of the tissue guard within an access device or natural body orifice and a second, expanded configuration to facilitate engagement of the at least two petals beneath the access device or within the natural body orifice to secure the tissue guard therein.

2. The tissue guard according to claim 1, wherein at least one of the petals includes a grounding plate operably associated with the at least one the petal.

3. The tissue guard according to claim 2, wherein the grounding plate is affixed to the at least one petal by a rivet, adhesive or complementary mechanically interfacing surfaces.

4. The tissue guard according to claim 1, wherein the first leg of at least one of the plurality of torsion springs is operably received within a corresponding channel defined within the elongated body.

5. The tissue guard according to claim 1, wherein the second leg of at least one of the plurality of torsion springs is operably received within a corresponding channel defined within one of the at least two petals.

6. The tissue guard according to claim 1, wherein each of the at least two petals is operably engaged to at least two torsion springs.

7. The tissue guard according to claim 1, wherein the at least two petals are configured to overlap one another when moved to the first, compressed configuration.

8. The tissue guard according to claim 1, wherein at least one of the at least two petals is shaped like a duck bill to facilitate insertion within the access device or natural body orifice.

9. A tissue guard, comprising:
   an elongated body including a proximal end and a distal end and defining a lumen through the elongated body;
   a plurality of torsion springs, each torsion spring including a first leg, a second leg, and a spring defined between the first leg and the second leg, the first leg of each torsion spring seated within a channel defined within the distal end of the elongated body; and
   at least two petals extending from the distal end of the elongated body, each petal including a corresponding channel configured to seat the second leg of each respective torsion spring of the plurality of torsion springs, wherein the petals are movable between a first, compressed configuration to facilitate insertion of the tissue guard within an access device or natural body orifice and a second, expanded configuration to facilitate engagement of the at least two petals beneath the access device or within the natural body orifice to secure the tissue guard therein.

10. The tissue guard according to claim 9, wherein at least one of the at least two petals includes a grounding plate adapted to connect to a remote ground of an electrosurgical system.

11. The tissue guard according to claim 10, wherein the grounding plate is disposed on one surface of the at least one petal and a rivet is disposed on an opposite surface of the at least one petal, the rivet configured to connect the grounding plate to the at least one petal.

12. The tissue guard according to claim 11, wherein both the grounding plate and rivet provide a local ground to the electrosurgical system.

13. The tissue guard according to claim 11, wherein the rivet is exposed on an outer surface of the at least one petal and the grounding plate is disposed on an underside of the at least one petal.

14. The tissue guard according to claim 11, wherein the grounding plate is substantially flush with the one surface of the at least one petal and the rivet is substantially flush with the opposite surface of the at least one petal.

15. The tissue guard according to claim 9, wherein the at least two petals are configured to overlap one another when moved to the first, compressed configuration.

16. The tissue guard according to claim 9, wherein at least one of the at least two petals is shaped like a duck bill to facilitate insertion within the access device or natural body orifice.

\* \* \* \* \*